US005459043A

United States Patent [19]
Brown

[11] Patent Number: 5,459,043
[45] Date of Patent: Oct. 17, 1995

[54] HYBRIDOMA CT43 PRODUCING A MONOCLONAL ANTIBODY TO A NOVEL MUCIN EPITOPE WHICH CORRELATES WITH THE PRESENCE OF COLORECTAL CANCER

[75] Inventor: Joseph P. Brown, Seattle, Wash.

[73] Assignee: Genetic Systems Corporation, Redmond, Wash.

[21] Appl. No.: 985,524

[22] Filed: Dec. 3, 1992

Related U.S. Application Data

[63] Continuation of Ser. No. 407,513, Sep. 15, 1989, abandoned.

[51] Int. Cl.$^6$ .................. G01N 33/574; G01N 33/53; C07K 16/30
[52] U.S. Cl. .............. 435/7.23; 435/7.1; 435/7.9; 435/7.92; 435/172.2; 435/240.27; 436/64; 436/813; 530/387.7; 530/388.8; 530/388.85; 530/389.7; 530/395
[58] Field of Search .............. 530/387.7, 388.8, 530/388.85, 389.7, 395; 435/7.23, 7.1, 7.9, 7.92, 172.2, 240.27; 436/64, 813, 518, 536, 540

[56] References Cited

U.S. PATENT DOCUMENTS

| | | | |
|---|---|---|---|
| 4,349,528 | 9/1982 | Koprowski et al. | 424/12 |
| 4,486,530 | 12/1984 | David et al. | 436/519 |
| 4,743,543 | 5/1988 | Kortright | 435/29 |
| 4,803,169 | 2/1989 | Linsley et al. | 436/501 |
| 4,863,854 | 9/1989 | Mattes et al. | 435/7.23 |
| 4,900,684 | 2/1990 | Hansen | 435/7.94 |
| 4,921,789 | 5/1990 | Salem et al. | 435/172.2 |

FOREIGN PATENT DOCUMENTS

| | | |
|---|---|---|
| 0200464 | 11/1986 | European Pat. Off. . |
| 0313244 | 4/1989 | European Pat. Off. . |
| 0316764 | 5/1989 | European Pat. Off. . |
| 8600414 | 1/1986 | WIPO . |
| 8910563 | 11/1989 | WIPO . |

OTHER PUBLICATIONS

Watanabe, M., et al., Jpn. J. Cancer Res. (Gann), vol. 76, Jan. 1985, pp. 43–52.
Kellokumpu, I. et al., Br. J. Cancer, vol. 55(4), 1987, pp. 361–366.
Ogasawara, M., et al., Biological Abstracts, vol. 85(7), Abstract No. 70236, 1988.
Hakomori, Ann. Rev. Immunol. 2:103–26 (1984).
Herlyn et al., Proc. Natl. Acad. Sci. USA 76:1438–1442 (1979).
Linsley et al., Cancer Res. 46:5444–5450 (1986).
Magnani et al., J. Biol. Chem. 257:14365–14369 (1982).
Magnani et al., Cancer Res. 43:5489–5492 (1983).
Mercer et al., Clin. Chem. 31:1824–1828 (1985).
Nudelman et al., J. Biol. Chem. 257:12752–56 (1982).
Rittenhouse et al., Lab. Med. 16:556 (1985).

Primary Examiner—Toni R. Scheiner
Attorney, Agent, or Firm—Townsend and Townsend and Crew

[57] ABSTRACT

The present invention relates to a novel monoclonal antibody reactive with human colorectal mucin antigen. More particularly, the antibody of the invention is a murine monoclonal antibody, CT43, reactive with a novel antigenic determinant on much antigen highly correlated with human colorectal cancer. The antigenic determinant found by the CT43 has been characterized as neuraminidase and proteinase K resistant, periodate sensitive and unreactive with the glycoconjugates of Table 2. Methods are provided for the detection and quantitation of the CT43 antigenic determinant and its correlation with colorectal cancer. CT43, and CT66 specific for the sialylated Lewis a and Lewis a antigen have been deposited with the American Type Culture Collection, as accession numbers ATCC HB 10217 and ATCC HB 10218, deposited Sep. 6, 1989.

11 Claims, No Drawings

HYBRIDOMA CT43 PRODUCING A MONOCLONAL ANTIBODY TO A NOVEL MUCIN EPITOPE WHICH CORRELATES WITH THE PRESENCE OF COLORECTAL CANCER

This is a Continuation of application Ser. No. 07/407,513, filed Sep.15, 1989, now abandoned.

FIELD OF THE INVENTION

This invention relates to the hybridoma cell line CT43 which produces a monoclonal antibody reactive with mucins, particularly a novel epitope on mucin molecules associated with colorectal cancer malignancies. Monoclonal antibody CT43 and other antibodies specific for the epitope recognized by CT43 are useful in the detection and treatment of human cancers, particularly colorectal cancer.

BACKGROUND OF THE INVENTION

Mucins are heavily glycosylated, high molecular weight glycoproteins with a carbohydrate content of up to 80% that are secreted by epithelial tissues. Mucins have been identified as tumor-associated antigens and have been found to be released into the circulation in large amounts by most carcinomas
(Rittenhouse et al. *Lab. Med.* 16: 556 (1985), Magnani et al. *Cancer Res.* 43: 5489 (1983), Linsley et al. *Cancer Res.* 46: 5444 (1986), incorporated herein by reference).

The diagnosis of colorectal cancer is currently based upon clinical findings, detection of blood in fecal samples, and a correlation with high level of certain carcinoma- associated mucin antigens in tissue, blood, or serum samples detected by the binding of certain monoclonal antibodies. Examples of monoclonal antibodies which have been reported to recognize antigens associated with gastrointestinal or colorectal cancer include CA 19-9 (Magnani, J. L. et al. supra), CCK061 (European Patent Application, EP200464) and a monoclonal antibody specific for carcinoembryonic antigen (1116NS-3d), U.S. Pat. No. 4,349,528). In vitro diagnostic methods for detecting the presence of cancer cells or other cancer cells producing small intestine mucin antigens and/or large intestine mucin antigen and monoclonal antibodies useful therein are disclosed by Linnane (PCT Publication WO 86/00414). Many other malignant conditions are also detected, in addition to colorectal carcinoma (e.g., stomach, gall bladder, malignant lymphoma and acute lymphocytic leukemia). Diagnostic tests based on each of the antigens recognized by the above antibodies fail to have a high correlation with colorectal carcinoma, particularly in its early stages, resulting in high numbers of false positive results. The only truly reliable method to date is biopsy of potentially malignant growths. Monoclonal antibodies such as CEA or CA 19-9 are used in conjunction with other diagnostic methods or in post-therapy survey for cancer recurrance.

SUMMARY OF THE INVENTION

The present invention provides a monoclonal antibody that is highly reactive with mucin epitopes associated with human colorectal cancer. More specifically, the novel antibody of the invention, designated CT43, is a murine monoclonal antibody that binds a novel epitope on the membrane of colorectal carcinoma cells and also on mucin molecules found in human sera of patients suffering from colorectal cancer. The novel mucin epitope is characterized as being neuraminidase and proteinase K resistant, periodate sensitive and unreactive with many known, naturally occuring glycoconjugates.

Further, methods are provided for the use of novel monoclonal antibodies of the present invention for the detection or quantitation of an epitope associated with colorectal cancer. Detection of colorectal cancer associated mucin can be used for the diagnosis of colorectal cancer and the assessment of patients following various treatments for cancer recurrance. The method comprises the steps of incubating the sample with one or more monoclonal antibodies specific for the epitope correlated with colorectal cancer associated mucin, wherein the antigenic determinant is neuraminidase and proteinase K resistant, periodate sensitive and unreactive with the glycoconjugates of Table 2, and either simultaneously or sequentially, with a labeled antibody composition which specifically binds with an antigenic determinant common to mucins, such that specific binding occurs, thereby forming a reaction complex and detecting the complex formed in the previous step to determine the amount of label associated with the reaction complex and thereby detecting or quantitating the amount of colorectal cancer associated mucin present in the sample. In a preferred embodiment murine monoclonal antibody CT43 is immobilized on the surface of a microtiter plate well. The quantity of colorectal cancer associated mucin in a blood serum sample is detected by the formation of a reaction complex between the immobilized CT43 and the colorectal cancer associated mucin in the serum sample. Complex is detected by the binding of horseradish peroxidase conjugated monoclonal antibody CT66 binding with the reaction complex. CT66 is specific for Lewis a and sialylated Lewis a antigen.

Also, the present invention provides kits for the detection or quantitation of colorectal cancer associated mucin epitope bound by CT43. The kits are composed of compartments containing a first monoclonal antibody which specifically binds the CT43 epitope and a second monoclonal antibody composition which specifically binds with an antigenic determinant common to mucin molecules, and labels providing for a detectable signal covalently bonded to the second antibody composition on bonded to antibodies reactive with the second antibody composition.

CT43 may also be useful for particular therapeutic applications. The antibody may be used as a component of various immuno-conjugates including antibody-drug and antibody-toxin conjugates or radiolabeled to deliver radioisotope to tumors. CT43 may also be therapeutically useful in an unmodified form.

DESCRIPTION OF THE SPECIFIC EMBODIMENTS

In accordance with the present invention novel compositions of a monoclonal antibody, CT43, specific for a novel mucin epitope is provided wherein such antibody is capable of specifically binding an epitope of carcinoma-associated mucin which correlates with the presence colorectal cancer. Monoclonal antibodies and fragments thereof may be utilized as diagnostic or therapeutic reagents.

The CT43 antibody can be used to isolate and characterize the antigen to which it binds. Use of monoclonal antibodies as probes to identify and characterize the epitopes they recognize and to further define the cell membrane antigens to which it reacts can be found, for example, in Nudeleman et al. *J. Biol. Chem.* 257: 12752–56 (1982) and Hakomori. *Am. Rev. Immunol.* 2: 103–26 (1984). Results of preliminary epitope screens on common glycoconjugates have not revealed the epitope to which CT43 binds.

The monoclonal antibody of the present invention can be prepared by immortalizing the expression of nucleic acid sequences which code for antibodies specific for epitopes of carcinoma-associated mucin antigens recognized by CT43. This may be accomplished by introducing such sequences, typically cDNA encoding for the antibody, into a host capable of cultivation and culture. The immortalized cell line may be a mammalian cell line that has been transformed through oncogenesis, by transfection, mutation, or the like. Such cells include myeloma lines, lymphoma lines, or other cell lines capable of supporting the expression and secretion of antibody in vitro. The antibody may be a naturally occurring immunoglobulin of a mammal other than human, produced by transformation of a lymphocyte, by means of a virus or by fusion of the lymphocyte with a neoplastic cell, e.g., a myeloma, to produce a hybrid cell line. Typically, the lymphoid cell will be obtained from an animal immunized against carcinoma-associated mucin antigen or a fragment thereof containing an epitopic site recognized by CT43 with a high correlation with colorectal cancer.

Immunization protocols are well know in the art and can vary considerably yet remain effective. See Goding, *Monoclonal Antibodies:* Principle and Practice, (1983) which is incorporated herein by reference. Immunogenic amounts of antigenic preparations of partially purified carcinoma-associated mucin preparations are injected, generally at concentrations in the range of 1 ug to 20 mg/kg of host. The partially purified carcinoma-associated mucin may be administered once or a plurality of times, usually at one to four week intervals. Immunized animals are monitored for production of antibody to carcinoma-associated mucin antigen, the spleens are then removed and splenic B lymphocytes isolated and transformed or fused with a myeloma cell line. The transformation or fusion can be carried out in conventional ways, the fusion technique being described in an extensive number of U.S. patents, e.g., U.S. Pat. Nos. 4,172,124; 4,350,683; 4,363,799; 4,381,292; and 4,423,147. See also, Kennett et al. *Monoclonal Antibodies* (1980) and references therein, and Goding, supra.

The hybrid cell lines may be cloned and screened in accordance with conventional techniques, and antibodies in the cell supernatants detected that are capable of binding partially purified carcinoma-associated mucin. The appropriate hybrid cell lines may then be grown in large scale culture in vitro or injected into the peritoneal cavity of an appropriate host for production of ascites fluid. By virtue of having the antibody of the present invention, CT43, which is known to be specific for a carcinoma-associated mucin epitope with a high correlation with colorectal cancer, the supernatants may be screened in competition with other monoclonal antibodies in a competitive assay. Examples of such competitive binding assays may be found in, for example, U.S. Pat. No. 4,803,169. The antibody of the present invention may also be used to affinity purify colorectal carcinoma-associated mucin to be used as an immunogen to potentially increase the probability of obtaining a monoclonal antibody competitive with CT43 in binding assays.

Thus, hybrid cell lines can be readily produced from a variety of sources based on the availability of the present antibody specific for the particular novel epitopes. Alternatively, this hybrid cell line may be fused with other neoplastic B cells, or such other B cells may serve as recipients for genomic DNA coding for the antibody. Or, using hybrid DNA techniques, the monoclonal antibody may be an immunoglobulin produced by inserting genomic DNA or cDNA coding for one or both heavy and light chains into an expression vector for expression of the chains. See, for example, European Patent Publication Nos. 171,496 and 173,494.

While rodent, particularly murine neoplastic B cells are preferred, neoplastic cells from other mammalian species may be employed, such as lagomorpha, bovine, ovine, equine, porcine, avian or the like. Immunization of these animals can be readily performed and their lymphocytes, particularly, splenocytes, may be obtained for fusions.

The monoclonal antibodies secreted by the transformed or hybrid cell line may be of any of the classes or subclasses of immunoglobulins, such as IgM, IgD, IgA, or subclasses of IgG known for each species of animal. As IgG is the most common isotype utilized in diagnostic assays, it is preferred for this purpose. The monoclonal antibodies may be used intact, or as fragments, such as Fv, Fab, $F(ab')_2$, but usually intact.

Monoclonal antibodies of the present invention are particularly useful for monitoring return to the disease state and in conjunction with other tests for diagnostic purposes. Typically, the assay will entail the detection of the of a reaction complex formed through the binding of the monoclonal antibody to a particular epitope or a carcinoma-associated mucin antigen. Hybridomas producing monoclonal antibodies capable of blocking the binding of antibodies produced by the hybrid cell line of the present described below are preferred.

For use in immunoassays the antibodies of the present invention typically entail the the detection of immune complexes formed between the capture monoclonal antibody and the carcinoma-associated mucin antigen having epitopes highly correlated with colorectal cancer. Generally, to provide for detection the antibodies may either be labelled or unlabeled. A wide variety of labels may be employed, such as radionuclides, fluorescers, enzymes, enzyme substrates, enzyme cofactors, enzyme inhibitors, ligands (particularly haptens), etc.

Numerous types of immunoassays are available, and by way of example, some include those described in U.S. Pat. Nos. 3,817,827; 3,850,752; 3,901,654; 3,935,074; 3,984,533; 3,996,345; 4,034,074; 4,098,876; and 4,376,110, all of which are incorporated herein by reference. When unlabeled, detection can be accomplished in agglutination assays. In addition, unlabeled antibody compositions can be used in combination with other labeled antibodies (second antibodies) that are reactive with the carcinoma-associated mucin antigens, such as CT66 specific for Lewis a and sialylated Lewis a (ATCC HB10218 deposited Sep. 6, 1989 with the American Type Culture Collection, Rockville, Md., 20852)

In general, it is necessary to at least partially purify the monoclonal antibody from the ascites fluid or culture supernatants before labeling. Methods of purification are well known and can include, for example, ammonium sulfate precipitation, ion exchange chromatography, or some combination thereof.

The monoclonal antibodies of the present invention find particular use in sandwich enzyme immunoassays to capture and detect carcinoma-associated mucin antigen having the CT43 epitope. A biological sample suspected of containing carcinoma-associated mucin antigens is combined with the subject monoclonal antibodies, which may first be attached to a solid support. The sample is then reacted with the monoclonal antibody under conditions conducive to immune complex formation and binding occurs between the antibodies and those molecules exhibiting the CT43 carcinoma-associated mucin epitope. The immune complexes may then be separated from uncomplexed material and, then if the capture antibody is labeled, immune-complex is detected. If the capture antibody is unlabeled, a second antibody, which may be a monoclonal antibody of the present invention, polyclonal antibody to carcinoma-associated mucin antigen, or an antibody to the capture antibody, and may be labeled or unlabeled, is added. If the second antibody composition is labelled the presence of the antibody labeled conjugate specificity bound to the epitopes is determined. In a convenient embodiment, the second antibody is labeled, and may be incubated simultaneously with the sample and capture antibodies. If the second antibody composition is unlabeled, a third antibody composition conjugated to a label may be used. Other conventional techniques well know to those skilled in the art may also be utilized.

In a particularly preferred embodiment, a method for determining the level of CT43 carcinoma-associated mucin epitope is carried out by incubating a monoclonal antibody of the present invention with a biological sample, and detecting the presence of immune complexes formed between the monoclonal antibody and the quantity of CT43 carcinoma-associated mucin epitope determined. Detection of immune complexes is by a labeled second antibody specific for a common mucin antigen CT66 which binds, Lewis a or sialylated Lewis a. The level of CT43 carcinoma-associated mucin epitope and the correlation with colorectal cancer determined.

The biological sample tested for the level of CT43 carcinoma-associated mucin epitope may comprise a physiological fluid, such as human serum or plasma, human tissues, or cell culture supernatants, or the like.

The capture antibody may be immobilized to a solid support in a variety of ways familiar to those skilled in the art. The support may include, but is not limited to, polytyrenes, polyacrylamides, silica, agarose, nitrocellulose, and the like. The supports may take the form of tubes, microwell plates, slides, beads, filters, etc. Latexes of polystyrene, polyacrylamides, silica, and the like may also be used.

The labeled antibody composition may be a polyclonal antiserum obtained from animals (e.g., rabbits, goats, or mice) immunized with carcinoma-associated mucin or fragments thereof by methods known to one skilled in the art. Monoclonal antibodies specific for antigens common to carcinoma-associated mucin antigens may also be used, i.e., Lewis a, Lewis x.

Biological fluids or samples may also be directly examined for CT43 carcinoma-associated mucin epitope by first affixing the specimen to a solid support, which may be accomplished in a variety of ways. Polystyrene can be used as a solid support (e.g., as microwell plats) or, alternatively, the sample may be attached to other solid supports including glass, nylon, cellulose acetate, nitrocellulose or other membranes as well as polyacrylamide, etc. The affixed samples are incubated with the desired monoclonal antibody or with a composition comprised of a monoclonal antibody of the present invention under conditions conducive to immune complex formation. The antigen-antibody complex is then washed and signal detected when a primary antibody is used. If the first antibody is unlabeled, a second labeled immunoglobulin- specific antibody is added. Thereafter, the presence of the label specifically bound to the antigen-antibody complex is determined.

Kits can also be supplied for use with the subject monoclonal antibodies in the detection and/or quantitation of carcinoma-associated mucin antigen having the CT43 epitope. Thus, the subject monoclonal antibody composition may be provided, usually absorbed to a solid phase or in a lyophilized form, either alone or in a conjunction with additional antibodies specific for malignant colorectal disease. The antibodies, which may be conjugated to a label or unconjugated, are included in the kits with buffers, such as Tris, phosphate, carbonate, etc., stabilizers, biocides, inert proteins, e.g. bovine serum albunun, or the like. Generally, these materials will be present in a total amount of at least about 0.001% wt. based again on the antibody concentration. Frequently, it will be desirable to include an inert extender or excipient, where the excipient may be present in from about 1 to 99% wt of the total composition. Where a second antibody broadly reactive with carcinoma-associated mucin is employed, this will usually be present in a separate vial. The second antibody is typically conjugated to a label and formulated in an analogous manner with the antibody formulations above. Standards of plural effusion from colorectal cancer patients of known reactivity in the assay is also provided in separate vials to establish a standard curve used to quantitate the level of antigen in a sample. The kits themselves comprise compartments containing vials or other containers for the reagents described above which are necessary for the performance of the particular diagnostic immunoassay. Such kits may find considerable utility in diagnosing colorectal cancer or monitoring the recurrence of colorectal associated malignant disease following surgery, radiotherapy, chemotherapy or combinations thereof.

Monoclonal antibody of the present invention may be used to purify and characterize the antigenic determinant for which it is specific. Antigen may be partially purified from a tumor source such as tumor cell lysates by such as gel exclusion chronotography. Fractions which contain high molecular weight mucin molecules are pooled and concentrated by any of several known methods. Pooled fractions are then run onto an affinity column comprising monoclonal antibody of the present invention conjugated to the column matrix. Activated column materials, such as CNB activated sepharose or 1,1' carbonyldiimidazole-activated affinity matrix may be used. Bound antigen is eluted from the affinity column after unbound material has been washed from the column matrix. Fractions are assayed for the presence of protein and binding by the monoclonal antibody. Polyacrylaride gel electrophosesis followed by Western Blot may be used to test for antibody binding or small aliquots from the collected fractions maybe tested by ELISA to determine the fractions containing antigens of interest. The fractions of interest are then pooled and concentrated for further characterization.

Other features and advantages of the present invention will become apparent from the following experimental descriptions, which describe the invention by way of example. The examples are offered by way of illustration and not by way of limitation.

EXAMPLE I

PURIFICATION OF CARCINOMA-ASSOCIATED ANTIGEN

Collection of Pleural Effusion Fluids

Effusion fluids used contained predominantly a soluble form of mucin. Pleural effusions (GI-PE) were obtained from Gastrointestinal cancer patients at Virginia Mason Clinic in Seattle, Wash. Effusion samples were stored frozen at −20° C.

Purification of Colon Adenocarcinoma Carcinoma-Associated Mucin (CAM)

Pools of carcinoma-associated mucin were purified from acid-ethanol extracted colon adenocarcinoma. Surgical specimens were pooled and stored at −70° C. Tumor tissue samples (31.7 g) were thawed in a volume of 125 ml of extraction buffer (95% ethanol, 100 mM HCl, phenylmethyl- sulfonyl fluoride (32 ug/ml), Aprotinin (2 mg/ml), and the mixture was stirred for 16 hours at 4° C. Insoluble material was collected by sedimentation at 10,000×g for 30 minutes at 4° C., resuspended in $H_2O$ at a concentration of approximately 4 g/ml (weight/volume) and guanidine HCl was immediately added to a final concentration of 6M. The mixture was vortexed vigorously and allowed to stand overnight at 4° C., then sedimented at 1,000×g for 10 minutes, and the supernatant was then collected, following removal of the lipid phase.

Equilibrium sedimentation in cesium chloride (CsCl) density gradients was performed. CsCl (source) was added at 0.6 g/ml (original volume) and the density was adjusted to 1.33–1.35 g/ml, measured gravemetrically. Samples were then centrifuged in a Beckman 50.2 rotor at 40,000 rpm (145,500×g average) for 60 to 65 hours at 21° C. Fractions were dialyzed against $H_2O$ and then assayed for by polyacrylamide gel electrophoresis.

Further purification was carried out by Column chromatography using either a TSK-G3000SW or TSK-64000SWG column. Phosphate buffer (50 mM, pH 7.5) was used to elute colon adenocarcinoma mucin from the column. Fractions containing molecules of over 200,000 MW were collected as determined by protein standards under similar conditions.

EXAMPLE II

GENERATION AND SCREENING OF MONOCLONAL ANTIBODIES

Generation of Monoclonal Antibody CT43

Hybridomas producing novel monoclonal antibody CT43 were developed by immunizing Balb/c mice interperitoneally with an injection of 200 ul of cesium chloride gradient purified colorectal adenocarcinoma mucin with 1 mg silica as adjuvant. Fourteen days later, 140 ul of column chromatography purified mucin was injected subqutaneously with 1 mg of silica as adjuvant. Column chromatography purified mucin was used as the immunogen for subsequent immunizations on days 28 (500 ul), 35 (200 ul) and 84 (200 ul). On day 171 pleural effusion mucin (350 ul) colorectal carcinoma associated mucin (100 ul), and 200 ul of column chromatography purified mucin were used for the final booster immunization. Silica was used as adjuvant for all immunizations. Spleens were removed from mice which gave a positive immune response on purified colorectal mucin 3–4 days following the final booster injection.

Fusions were carried out generally following the procedures outlined by Kohler and Milstein, supra. In brief, mononuclear cells from one spleen and five lymph nodes of a mouse were combined in a 1:1 ratio with log phase NS-1 mouse myeloma cells and fused with polyethylene glycol. The final hybrid cell suspension was diluted to a concentration of $1\times10^3$ cells/ml in IMDM-HAT containing 15% fetal calf serum, 1 mM sodium pyruvate, 100 ug/ml streptomycin and 100 IU/ml penicillin, $1.0\times10^{-4}$M hypoxanthine, $4.0\times10^{-7}$M aminopterin, and $1.6\times10^{-5}$M thymidine) which included $2.5\times10^7$ balb/c thymocytes as feeder cells. The mixture was plated (200 ul per well) into 96 well microtiter plates. Cultures were fed by the removal and replacement of half of the volume of each well with fresh IMDM-HAT every two-three days. Culture supernatants were assayed for the presense of antibody to purified colorectal carcinoma associated mucin by enzyme-linked immunosorbent assay (ELISA) when cell growth reached approximately 40% confluency in the wells, 7–10 days after fusion. Protocols used for screening and characterizing the cell lines for the production of monoclonal antibody for CT43 are further described below.

Generation of Monoclonal Antibody CT66

Hybridomas producing monoclonal antibody CT66 were developed by immunizing Balb/c mice interperitoneally with an injection of 200 ul of cesium chloride gradient purified colorectal adenocarcinoma mucin with 1 mg silica as adjuvant. Fourteen days later, 140 ul of column chromatography purified mucin was injected subcutaneously with 1 mg of silica as adjuvant. Column chromatography purified mucin was used as the immunogen for booster immunizations on days 28 (500 ul), 35 (200 ul), and 84 (200 ul). On day 171 pleural effusion mucin (350 ul), colorectal carcinoma associated mucin (100 ul), and 200 ul of column chromatography purified mucin were used for the final booster immunization. Silica was used as adjuvant for all immunizations. Fusions were carried out generally as described above.

Screening

Various screening procedures were used to isolate monoclonal antibodies CT43 and CT66 which specifically bind epitopes associated with certain mucins. Clones were initially screened for binding to purified colorectal adenocarcinoma mucin (CAM) purified by column chromatography in an ELISA assay.

CAM was diluted 1:100 in BSA-Tris Buffer and 50 ul added to wells of microtiter plates. Immobilization was allowed to occur for at least one hour at room temperature before the excess was removed and the wells blocked with bovine serum albumin/Tris buffer for 1 hour at room temperature. Hybridoma supernatant (60 ul) to be screened was added per well and incubated for 1 hour at room temperature prior to the addition of goat anti-mouse IgG horseradish peroxidase conjugate (1:1000) and goat anti-mouse IgG and IgM horseradish peroxidase conjugate (Cappel, 1:2000). Dilution was carried out in 10% fetal calf sera/phosphate buffered saline. Conjugate was allowed to react with immobilized hybridoma antibody for 30 minutes at room temperature. Tetramethylbenzidine was used as the enzyme substrate for the detection of positive wells. Reaction was terminated with the addition of 1N sulfuric acid. Between each addition step wells were washed with 10% FCS/PBS.

Clones providing positive reactions were expanded and retested on GI-pleural effusion (GI-PE) mucin ELISA similar to that provided above. Clones which produce monoclonal antibodies highly reactive with colorectal cancer associated mucin and pleural effusion for gastrointestinal cancer patients were than used to configure double antibody determinant assays described below.

Isotype Determination 96-well plates were coated with CAM mucin as described above. Fifty ul of supernatant cultures of the CT43 cell line was added and incubated at room temperature for 1 hour. Well were again washed and monospecific goat anti-mouse immunoglobulin-horseradish peroxidase conjugate (1:2000 in 10% FCS/PBS, Cappel Laboratories) was added to the wells for 30 minutes at room temperature Wells were again washed and tetramethylbenzidine substrate was added to each well for 15 minutes. The reaction was stopped by the addition of 1N sulfuric acid and the optical density determined with an automatic plate reader 450 nm.

Based on these procedures CT43 was determined to produce monoclonal antibody of the IgG2b isotype.

Specificity of Monoclonal Antibody CT43

Binding specificity and correlation with colorectal cancer was determined by testing blood samples from individuals having malignant disease by double determinant ELISA. Monoclonal antibody CT43 was used as the capture antibody wherein CT43 was immobilized in the wells of a 96 well microtiter plate. Serum or plasma from an individual to be tested was diluted in 1:2 dilution buffer 0.05M HEPES, 0.15M NaCl, 20% FCS and 50 ul added to each well. After incubation for 1 hour and washing a second monoclonal antibody, CT66 specific for sialylated Lewis a and Lewis a antigen, was conjugated with horseradish peroxidase by the method of Nakane et al *J. Histochem. Cytochem.* 22: 1084 (1974). Conjugate was diluted 1:2 in 0.05M HEPES, 0.15M NaCl, 20% FCS and 500 ul was added to each well and allowed to incubate for 60 minutes at room temperature. 3,3'5,5' tetramethylbenzidine in citrate/phosphate buffer, pH 6.0 with 0.0015% hydrogen peroxide was added and after 15 minutes 1N sulfuric acid was added to stop the reaction. Optical density at 450 mm was determined. Blood samples were from a group of patients characterized by the presence of absence of colorectal cancer. Patients were grouped as Normal, Benign, Local/Regional or Metastatic based on status of disease progression.

Monoclonal antibody CA 19-9 was tested by the methods as described by the manufacturer, Centor. CEA was tested by the methods as described by the manufacturer, Abbott Laboratories.

Table 1 compares the ability of antibodies CT43, CEA and CA 19-9 to detect and diagnose colorectal cancer. CT43 was determined to be better able to detect colorectal cancer at its early stages than CEA and CA 19-9 and to be at least as good as CEA and better than CA 19-9 at detecting later stages.

tion. Sensitivity or resistance to Neuraminidase, Proteinase K and periodate indicate whether the antigenic determinant may be at least partially protein in nature, involve one or more sialic acid residues or other carbohydrate moeities.

Colorectal cancer associated mucin was immoblized in microtiter wells (Immulon II) previously treated with 20 ug/ml poly-L-lysine in PBS, overnight at 4° C. Excess mucin was removed and wells were blocked with 2% BSA/Tris for 1 hour at 37° C. Wells containing immobilized mucin were treated for 1 hour at 37° C with either a) 20 mU/ml *C. perfringens* neuraminidase type X in 0.15M NaCl, 50 mM acetate pH 5.0, 0.1% $CaCl_2$, b) 200 mU/ml proteinase K in PBS or c) 0.5% $NaIO_4$ in PBS. Wells teated with $NaIO_4$ were post incubated with 2M sodium metabisulfite. Following treatment the wells were washed with PBS prior to the addition of 50 ul of CT43 cell supernantant or diluted ascites for 2 hours at room temperature. Wells were washed twice with PBS and CT43 antibody binding was detected by the addition of 1:2000 dilution of goat anti-mouse IgG and IgM-horseradish peroxidase conjugate in 20% FCS/PBS for 30 minutes at room temperature. Wells were washed with PBS and tetramethylbenzidine substrate was added for 30 minutes. The color reaction was stopped with the addition of 1N $H_2SO_4$ and the optical density at 450 nm determined.

The CT43 antigenic determinant was determined to be resistant to neuramimidase and proteinase K, and sensitve to periodate. Therefore, the antigenic determinant is unlikely to involve sialic acid residues and does not appear to be protein in nature. Sensitivity to treatment with periodate appears to indicate the antigenic determinant is carbohydrate in nature.

Further analysis of the antigeinc determinant recognized by CT43 was carried out by testing the binding of CT43 to various glycoconjugates including glycolypids isolated and purified from natural sources and synthetic glycoproteins. Glycolipids were separated by thin layer chromatography as described by Magnani et al. *J. Biol. Chem.* 257: 14365 (1982). Briefly, chromatograms of separated glycolipids were overlayed with a monoclonal anitbody followed by $I^{125}$ labeled anti-mouse immunoglobulin. Antibody bound to a glycolipid antigen on the chromatogram was detected by exposure to x-ray film. About 10 mg of glycolipid antigen can usually be detected by this method. Sources of naturally occurring glcolipids included the Folch upper phase extract

TABLE 1

| | TESTING OF BLOOD SERUM SAMPLES BY MONOCLONAL ANTIBODY ELISA | | | | | | |
|---|---|---|---|---|---|---|---|
| | | CT43 | | CEA | | CA19-9 | |
| | TOTAL | HIGH | PERCENT | HIGH | PERCENT | HIGH | PERCENT |
| Normal | 92 | 1 | 1.1 | 0 | 0.0 | 1 | 1.1 |
| Benign | 103 | 3 | 2.9 | 5 | 4.9 | 3 | 2.9 |
| Local/Regional | 94 | 25 | 26.6 | 19 | 20.2 | 11 | 11.7 |
| Metastatic | 110 | 64[1] | 58.7 | 69 | 62.7 | 55 | 50.0 |

1. A total of 109 blood samples diagnosed with metastatic colorectal cancer were tested.

ANTIGEN CHARACTERIZATION

The antigenic determinant to which monoclonal antibody CT43 binds was determined initially by assessing the sensitivity of monoclonal antibody-antigen binding to treatment by protease glycosidase treatment and chemical modificaof bovine brain, total lipid extract of human kidney, total lipid extract of meconium, the upperphase extract of the SW1116 human colon carcinoma cell line, upper phase of sciatic nerve extract and purified sialylated $Le^a$-active hexasaccharide ceramide. A positive control of colorectal carcinoma mucin was run with the glycolipids and a duplicate chromatogram treated under identical conditions but without monoclonal antibody CT43 was run as a negative control.

Synthetic glycoproteins used to screen for CT43 binding contained 10–20 moles of purified oligosaccharide covalently coupled per mole of either human or bovine serum albumin. Three different chemical spacer arms were used to couple the oligosaccarides to proteins a) p-aminophenyl (PAP); b) aminophenylethyl (APE); and c) acetyl phenylene diamine (APD). Both PAP and APE attach the oligosaccharide to the protein glycosidically, retaining the anomeric configuration of the reducing sugar. APD, however, attaches the oligosaccharides to protein by reductive amination, thereby converting the reducing sugar to an aminoalditol.

Binding of CT43 to immobilized glycolipids and to synthetic glycoproteins was also examined by ELISA. Glycolipids were dried from methanol in microtiter wells at 100 mg/well. Synthetic glycoproteins were coated on the surface of microtiter well by incubation of glycoprotein diluted to 200 mg in PBS pH7.4/well. Purified CT43 was assayed at a concentration of 10 ug/ml in 0.01M Tris-HCl, pH 7.4, containing 1% BSA and antibodies of 1:100 in the same buffer.

Table 2 lists the glycolipids and synthetic glycoproteins tested. CT43 was not found to bind strongly to any of the glycoconjugates tested. Very weak reactivity was detected to H type 1 oligosacchride.

TABLE 2

GLYCOCONJUGATE TESTED FOR BINDING OF MONOCLONAL ANTIBODY CT43

| GLYCOLIPIDS | GLYCOPROTEINS |
|---|---|
| GM1 | Lacto-N-fucopentaose I-HSA[1] |
| GM2 | Lacto-N-fucopentaose II-HSA |
| GM3 | Lacto-N-fucopentaose III-HSA |
| GD1a | Lacto-N-difucohexose I-HSA |
| GD1b | Maltose-HSA |
| GD3 | Lactose-HSA |
| FF1b | Lacto-N-tetraose-HSA |
| GD3 | Lacto-N-neotetraose-HSa |
| G | Lacto-N-hexaose-HSA |
| GT16 | Lacto-N-neohexaose-HSA |
| Q1b | Meliboiose-HSA |
| H Type 1 | Cellobiose-HSA |
| H Type 2 | A-trisaccharide-HSA |
| A Type 1 | B-tetrasaccharide-HSA |
| CDH | A-tetrasaccharide-HSA |
| CTH | H-Type 2-HSA |
| Globoside | A-heptasaccharide-HSA |
| Forssman Glycolipid | Gangliotetraose-HSA |
| Le$^b$-Active Hexassacharide Ceramide | T-Antigen |
|  | 3' Sialylactose |
| Le$^y$-Active Hexasaccharide Ceramide | 6' Sialylactose |
|  | Sialyllacto-n-tetraose |
| Sialylated Le$^a$-Active Hexasaccharide Ceramide | Sialyllacto-N-tetraose b |
|  | Sialyllacto-N-tetraose c |
| B-Active Hexasaccharide Ceramide | Sialylated lacto-N-fucopentose II |
|  | Disialylated lacto-N-tertaose |
| Asialo GM1 | chitotriose |
| Asialo GM2 | Man$_3$GlcNAc |
| GD2 | Man$_2$GlcNAc |
| GT1a | Biantennery-octasaccharide |
|  | Globotriose |
|  | Globotetraose |
|  | Le$^y$-active hexasaccharide |
|  | Sialylated lacto-N-fucopentose III |

1. HSA is the abbreviation for Human serum albumin

What is claimed is:

1. A monoclonal antibody having specific immunologic reactivity with a mucin epitope associated with human colorectal carcinoma cells, said epitope being neuraminidase and proteinase K resistant, and which monoclonal antibody is produced by cell line ATCC HB 10217.

2. The cell line CT43 (ATCC HB 10217).

3. A method for the detection or quantitation of an epitope correlated with colorectal cancer in a biological sample, said method comprising:

a) incubating the sample with one or more capture antibodies each specific for an epitope correlated with colorectal cancer associated mucin, wherein said epitope is neuraminidase and proteinase K resistant and periodate sensitive and wherein at least one of the monoclonal antibodies is produced by cell line ATCC HB 10217, and either simultaneously or sequentially, with a labeled antibody composition binding to an antigenic determinant common to mucins such that specific binding occurs, thereby forming a reaction complex;

b) separating said reaction complex from unbound labeled antibody composition; and c) detecting the reaction complex formed in step (a) to determine the amount of label associated with the reaction complex and thereby detecting or quantitating the amount of colorectal cancer associated mucin present in the sample.

4. The method of claim 3, wherein the capture monoclonal antibodies are immobilized on a solid phase.

5. The method of claim 3, wherein the label is selected from the group consisting of radionuclides, fluorescers, enzymes, enzyme substrates, enzyme cofactors, enzyme inhibitors, and ligands.

6. The method of claim 3, wherein the labeled antibody composition is one or more monoclonal antibodies.

7. The method of claim 6, wherein the labeled monoclonal antibody is obtained from cell line CT66 (ATCC HB 10218).

8. The method of claim 3, wherein the biological fluid is selected from the group consisting of blood, serum, pleural effusion, and sputum.

9. A test kit for use in detecting the presence of colorectal cancer associated mucin, said kit comprising compartments containing a first monoclonal antibody composition, wherein said antibody composition comprises a monoclonal antibody which specifically binds an epitope on a mucin molecule correlated with colorectal cancer, said epitope being resistant to neuraminidase and proteinase K, sensitive to periodate, and wherein said first monoclonal antibody is produced by cell line ATCC HB 10217, and a second antibody composition which specifically binds with an epitope common to mucin molecules, and labels providing for a detectable signal covalently bonded to said second antibody composition or bonded to antibodies reactive with said second antibody composition.

10. The test kit of claim 9, wherein said second antibody is CT66.

11. The test kit of claim 9, wherein a known quantity of purified adenocarcinoma-associated mucin is provided in a separate compartment.

* * * * *